United States Patent [19]

Sugawara et al.

[11] Patent Number: 4,756,845

[45] Date of Patent: Jul. 12, 1988

[54] BLEACHING COMPOSITIONS

[75] Inventors: Hiroshi Sugawara; Yōji Tōma, both of Tokyo; Takahiro Takabe; Kenji Yokoi, both of Chiba, all of Japan

[73] Assignee: Lion Corporation, Tokyo, Japan

[21] Appl. No.: 867,513

[22] Filed: May 28, 1986

[30] Foreign Application Priority Data

| | | | |
|---|---|---|---|
| May 28, 1985 | [JP] | Japan | 60-114553 |
| Aug. 30, 1985 | [JP] | Japan | 60-191615 |
| Dec. 27, 1985 | [JP] | Japan | 60-299156 |
| Apr. 1, 1986 | [JP] | Japan | 61-75289 |

[51] Int. Cl.$^4$ ...................... C07D 213/84; C11D 3/28; C11D 3/395

[52] U.S. Cl. ...................................... 252/102; 252/95; 252/186.38; 252/541; 252/542; 252/545; 252/546; 546/286; 546/347; 546/348

[58] Field of Search ...................... 252/95, 102, 186.38

[56] References Cited

U.S. PATENT DOCUMENTS

| | | | |
|---|---|---|---|
| 2,612,898 | 10/1952 | Lorea | 134/2 |
| 2,927,840 | 3/1960 | Dithmar | 8/111 |
| 3,756,774 | 9/1973 | Kirner | 8/111 |
| 3,824,188 | 7/1974 | Loffelman | 252/95 |
| 3,862,200 | 1/1975 | Shepherd | 546/340 |
| 3,960,743 | 6/1976 | Nakagawa | 252/99 |
| 4,181,621 | 1/1980 | Raaf | 252/102 |
| 4,199,466 | 4/1980 | Benson | 252/95 |
| 4,248,928 | 2/1981 | Spadini | 428/286 |

*Primary Examiner*—Dennis Albrecht

*Attorney, Agent, or Firm*—Birch, Stewart, Kolasch & Birch

[57] ABSTRACT

A bleaching agent composition comprising a peroxide capable of releasing hydrogen peroxide in aqueous solution, in admixture with an activator for the peroxide selected from the group consisting of naphthonitriles, isophthalonitrides, terephthalonitriles, alkali metal salts of cyanic acid, cyanic acid ammonium salt, cyanopyridines and acid neutralized products thereof, cyanopyridinium salts, O-acyl compounds, and N-acyl compounds has improved bleaching power and enables bleaching of an article within a short period of time.

16 Claims, No Drawings

BLEACHING COMPOSITIONS

The present invention relates to a bleaching composition of the oxygen type comprising a peroxide capable of releasing hydrogen peroxide in aqueous solution, having improved bleaching power and finding a variety of applications in domestic and industrial uses.

BACKGROUND OF THE INVENTION

Bleaching agents are generally classified into reducing and oxidizing bleaching agents, among which the oxidizing bleaching agents are widely used because of their bleaching effect. The oxidizing bleaching agents are further classified into chlorine and oxygen types. Undesirably, the chlorine type bleaching agents cause discoloration of articles treated therewith so that they cannot be applied to colored clothes, and they have a disagreeable odor. The oxygen type bleaching agents are superior to the chlorine type bleaching agents in that they can be applied in a wider range of articles and they are free of an irritating smell and are easy to use.

Among the oxygen type bleaching agents, however, hydrogen peroxide and peroxides capable of releasing hydrogen peroxide in aqueous solution, for example, percarbonates, perborates, and hydrogen peroxide adducts of pyrophosphates, citrates, sodium sulfate, urea, and sodium silicate exhibit a lower bleaching action than the chlorine type bleaching agents. Further, the oxygen type bleaching agents cannot provide a sufficient bleaching effect within a short period of bleaching treatment and thus require a substantially extended period of time to achieve a sufficient bleaching effect, particularly at low temperatures.

It has also been a common practice to combine peroxides with bleaching activators, for example, certain O or N-acyl compounds such as tetraacetylethylenediamine (TAED), tetraacetylglycol uryl (TAGU), and pentaacetyl glucose (PAG) to obtain enhanced bleaching effect. These conventional bleaching activators, however, do not have a satisfactory activating effect and may even aid the bleaching agents to cause discoloration of articles treated therewith. For these and other reasons, the oxygen type bleaching agents have not gained a satisfactory beaching effect which is comparable to the chlorine type bleaching agents.

SUMMARY OF THE INVENTION

It is, therefore, an object of the present invention to provide a novel and improved oxygen type bleaching agent composition having enhanced bleaching effect and is capable of satisfactory bleaching articles within a relatively short treatment period.

Making extensive investigations on the enhancement of the bleaching power of oxygen type bleaching agents, we have found that the above object is attained by blending in a bleaching agent composition comprising a peroxide capable of releasing hydrogen peroxide in aqueous solution, a specific activator for the peroxide. More specifically, a remarkably enhanced bleaching power is obtained when the peroxide is used in combination with one or more members selected from compounds (A) through (J) as will be defined hereinafter.

According to the present invention, there is provided a bleaching agent composition comprising a peroxide capable of releasing hydrogen peroxide in aqueous solution, wherein the composition further comprises an activator for the peroxide, which is at least one member selected from the group consisting of the following compounds (A) through (J):

(A) naphthonitriles of the formula:

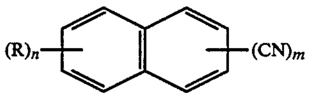

(1)

wherein R is a lower alkyl group or a lower alkoxy group n has a value from 0 to 4, m has a value from 1 to 4, and the sum of n and m is from 1 to 8, inclusive;

(B) isophthalonitriles of the formula:

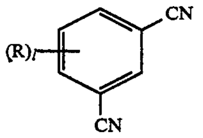

(2)

wherein R is as defined above, l has a value from 0 to 4;

(C) terephthalonitriles of the formula:

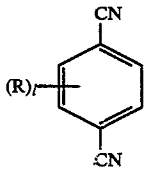

(3)

wherein R and l are as defined above;

(D) alkali metal salts of cyanic acid;

(E) cyanic acid ammonium salt;

(F) cyanopyridines of the formula:

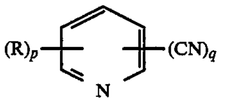

(4)

wherein R is as defined above, p has a value from 0 to 4, q has a value from 1 to 3, and the sum of p and q is from 1 to 5, inclusive;

(G) acid neutralized products of the cyanopyridines of formula (4);

(H) cyanopyridinium salts of the formula:

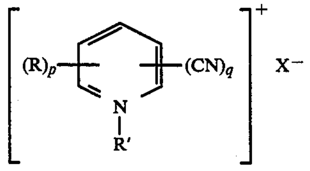

(5)

wherein R, p, and q are as defined above, R' is an alkyl or alkenyl group having 1 to 18 carbon atoms, and X is a halogen, an alkyl sulfonate group having 1 to 3 carbon atoms, or a phenyl sulfonate group;

(I) O-acyl compounds of the formula:

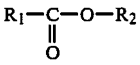
(6)

wherein $R_1$ is an alkyl or alkenyl group having 1 to 18 carbon atoms, $R_2$ is

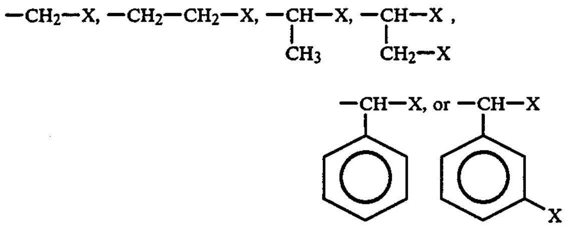

wherein X is an alkali metal salt of $—SO_3^-$, $—COO^-$ or $—SO_4^-$; and (J) N-acyl compounds of the formula:

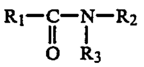
(7)

wherein $R_1$ and $R_2$ are as defined above, and $R_3$ is —H, $—CH_3$, $—C_2H_5$, $—C_3H_7$, $—CH_2OH$, $—C_2H_4OH$, or $—C_3H_6OH$.

The compositions of the present invention enable articles to be bleached within a relatively short period of time because the activating action of compounds (A) to (J) significantly improves the bleaching power of the peroxide which releases hydrogen peroxide in aqueous solution.

In addition to the bleaching power enhancement, particularly compounds (A) to (E) and (H) to (J) have the benefit of satisfactorily preventing discoloration of articles and compounds (F) and (G) provide improved bleaching effect even at relatively low temperatures.

The above and other objects, features and advantages of this invention will be more apparent from the following descriptions.

DETAILED DESCRIPTION OF THE INVENTION

The bleaching agent compositions of the present invention contain as a bleaching agent peroxides which release hydrogen peroxide in aqueous solution. Any peroxides may be used herein as long as they can release hydrogen peroxide when dissolved in water. Some preferred, nonlimiting examples of the peroxides include hydrogen peroxide, percarbonates, perborates, and hydrogen peroxide adducts of pyrophosphates, citrates, sodium sulfate, urea, and sodium silicate, and mixtures thereof. More preferred are hydrogen peroxide, percarbonates such as sodium percarbonate, and perborates such as sodium perborate monohydrate.

According to the present invention, one or more compounds selected from compounds (A) to (J) are used as an activator in combination with the aforementioned peroxides.

Preferred examples of naphthonitriles (A) of formula (1) include 1-naphthonitrile, 2-naphthonitrile, 1,3-dicyanonaphthalene, 1,6-dicyanonaphthalene, 1-cyano-2-methylnaphthalene, 1-cyano-2-methoxynaphthalene, etc., with 1-naphthonitrile and 2-naphthonitrile being most preferred. Preferred examples of isophthalonitriles (B) of formula (2) include isophthalonitrile, 1-methyl-2,4-dicyanobenzene, etc., with isophthalonitrile being most preferred. Preferred examples of terephthalonitriles (C) of formula (3) include terephthalonitrile, 1-methyl-2,5-dicyanobenzene, etc., with terephthalonitrile being most preferred.

Preferred examples of cyanic acid alkali metal salts (D) may include potassium cyanate, sodium cyanate, lithium cyanate, etc.

Preferred examples of cyanopyridines (E) of formula (4) include 2-cyanopyridine, 3-cyanopyridine, 4-cyanopyridine, 3-cyano-6-methylpyridine, 3-cyano-6-ethoxypyridine, etc. More preferred among them are 2-cyanopyridine, 3-cyanopyridine, and 4-cyanopyridine, with 2-cyanopyridine being most preferred. Acid neutralized products (G) of the cyanopyridines of formula (4) are acid neutralized products of the aforementioned cyanopyridines. Preferred are acid neutralized products of 2-cyanopyridine, 3-cyanopyridine, and 4-cyanopyridine, with the hydrochloric acid and sulfuric acid salts thereof being most preferred.

Preferred among cyanopyridinium salts (H) of formula (5) are 2-cyanopyridinium salts, 3-cyanopyridinium salts, and 4-cyanopyridinium salts of formula (5) wherein R' is an alkyl group having 1 to 12 carbon atoms. Examples of these salts are methyl-2-cyanopyridinium chloride, propyl-2-cyanopyridinium chloride, ethyl-3-cyanopyridinium bromide, ethyl-4-cyanopyridinium methylsulfonate, dodecyl-2-cyanopyridinium phenylsulfonate, etc.

Preferred among O-acyl compounds (I) of formula (6) are compounds (I-1) to (I-11) shown below:

(I-1) alkanoyloxymethane sulfonates of the formula:

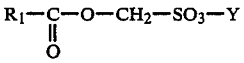

wherein $R_1$ is as defined above, and Y is an alkali metal;

(I-2) alkanoyloxyethane sulfonates of the formula:

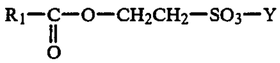

wherein $R_1$ and Y are as defined above;

(I-3) alkanoyloxymethylmethane sulfonates of the formula:

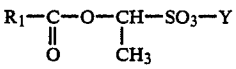

wherein $R_1$ and Y are as defined above;

(I-4) alkanoyloxyphenylmethane sulfonates of the formula:

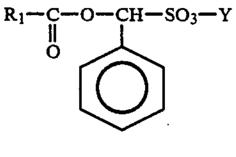

wherein $R_1$ and Y are as defined above;

(I-5) alkanoyloxy(benzene m-sulfonate)methane sulfonates of the formula:

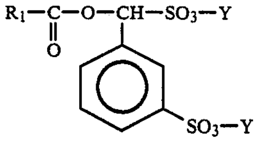

wherein $R_1$ and Y are as defined above;

(I-6) alkanoyloxymethane sulfates of the formula:

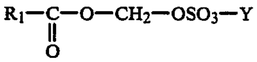

wherein $R_1$ and Y are as defined above;

(I-7) alkanoyloxyethane sulfates of the formula:

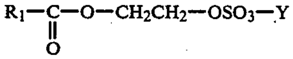

wherein $R_1$ and Y are as defined above;

(I-8) alkanoyloxyphenylmethane sulfates of the formula:

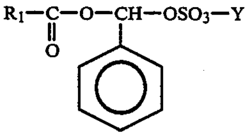

wherein $R_1$ and Y are as defined above;

(I-9) alkanoyloxymethane carboxylates of the formula:

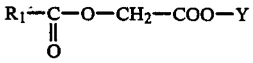

wherein $R_1$ and Y are as defined above;

(I-10) alkanoyloxyethane carboxylates of the formula:

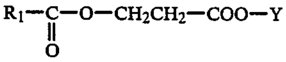

wherein $R_1$ and Y are as defined above; and (I-11) alkanoyloxysuccinates of the formula:

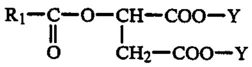

wherein $R_1$ and Y are as defined above.

Preferred among compounds (I-1) to (I-11) are alkanoyloxymethane sulfonates (I-1), alkanoyloxyethane sulfonates (I-2), alkanoyloxymethane sulfates (I-6), alkanoyloxyethane sulfates (I-7), alkanoyloxymethane carboxylates (I-9), and alkanoyloxyethane carboxylates (I-10), with those compounds wherein $R_1$ is an alkyl or alkenyl group having 1 to 12 carbon atoms being most preferred. The preferred alkali metal represented by Y is sodium.

Preferred among N-acyl compounds (J) of formula (7) are, for example, compounds (J-1) to (J-15) shown below:

(J-1) alkanoylaminomethane sulfonates of the formula:

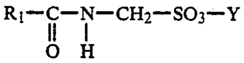

wherein $R_1$ and Y are as defined above;

(J-2) alkanoyl-N-methylaminomethane sulfonates of the formula:

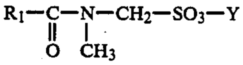

wherein $R_1$ and Y are as defined above;

(J-3) alkanoyl-N-ethylaminomethane sulfonates of the formula:

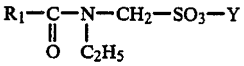

wherein $R_1$ and Y are as defined above;

(J-4) alkanoyltaurine salts of the formula:

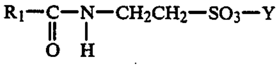

wherein $R_1$ and Y are as defined above;

(J-5) alkanoyl-N-methyltaurine salts of the formula:

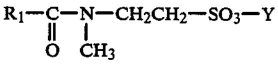

wherein $R_1$ and Y are as defined above;

(J-6) alkanoylaminomethylmethane sulfonates of the formula:

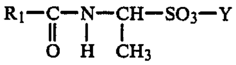

wherein $R_1$ and Y are as defined above;

(J-7) alkanoylamino(m-benzenesulfonate alkali metal)-methane sulfonates of the formula:

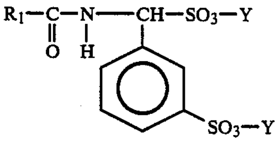

wherein $R_1$ and Y are as defined above;

(J-8) alkanoylaminomethane sulfates of the formula:

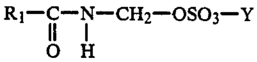

wherein $R_1$ and Y are as defined above;

(J-9) alkanoyl-N-methylaminomethane sulfates of the formula:

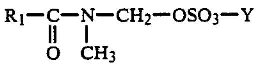

wherein $R_1$ and Y are as defined above;

(J-10) alkanoylaminoethane sulfates of the formula:

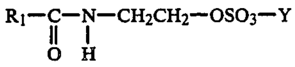

wherein $R_1$ and Y are as defined above;

(J-11) alkanoyl-N-methylaminoethane sulfates of the formula:

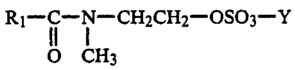

wherein $R_1$ and Y are as defined above;

(J-12) alkanoylaminomethane carboxylates of the formula:

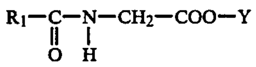

wherein $R_1$ and Y are as defined above;

(J-13) alkanoyl-N-methylaminomethane carboxylates of the formula:

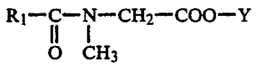

wherein $R_1$ and Y are as defined above;

(J-14) alkanoyl-N-ethanolaminomethane carboxylates of the formula:

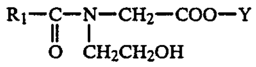

wherein $R_1$ and Y are as defined above; and (J-15) alkanoylaminoethane carboxylates of the formula:

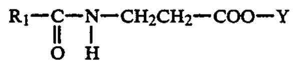

wherein $R_1$ and Y are as defined above.

Preferred among compounds (J-1) to (J-15) are alkanoylaminomethane sulfonates (J-1), alkanoyl-N-methylaminomethane sulfonates (J-2), alkanoyltaurine salts (J-4), alkanoylaminomethane carboxylates (J-12), and alkanoyl-N-methylaminomethane carboxylates (J-13), with those compounds wherein $R_1$ is an alkyl or alkenyl group having 1 to 12 carbon atoms and $R_3$ is —H or —$CH_3$ being most preferred. The preferred alkali metal represented by Y is sodium.

In the practice of the present invention, the peroxide and the activator are preferably blended in a molar ratio of from 20:1 to 1:2. A satisfactory bleaching power is at times not obtainable outside of this blending ratio range. The most preferred molar ratio of peroxide to activator ranges from 10:1 to 1:1.

The bleaching agent compositions of the present invention may be prepared in a conventional manner wherein any suitable well-known components may be added if desired. For example, the bleaching agent compositions of the present invention may be prepared by adding inorganic and organic builders, anionic and nonionic surfactants, enzymes, flavors, pigments, fluorescent agents, or the like to a blend of the peroxide and the activator. The inorganic and organic builders which may be used herein are sodium sulfate, sodium silicate, sodium tripolyphosphate, sodium ethylenediaminetetraacetate, sodium nitrilotriacetate, 1-hydroxyethane-1,1-diphosphonic acid and its salts, and the like. Examples of the anionic surfactants include sulfonates and sulfates having an alkyl group containing about 8 to about 22 carbon atoms, alkylbenzene sulfonates having an alkyl group containing about 9 to about 15 carbon atoms, sulfonates of α-olefins having about 8 to about 22 carbon atoms, and soaps of fatty acids having 10 to 22 carbon atoms. Preferred among these salts are alkali metal salts, especially sodium salts. Examples of nonionic surfactants include ethylene oxide condensates of alkyl phenols wherein 5 to 25 mols of ethylene oxide is condensed per mol of alkyl phenol having a straight or branched alkyl group containing about 6 to about 12 carbon atoms, ethylene oxide condensates of aliphatic alcohols wherein 5 to 30 mols of ethylene oxide is condensed per mol of aliphatic alcohol having a straight or branched chain containing about 8 to about 22 carbon atoms, nonionic surfactants commercially available under trade name "Pluronic" from Wyandotte Chem. and prepared by condensing propylene glycol with propylene oxide and further with ethylene oxide, mono- and diethanolamides of fatty acids wherein the acyl group contains about 8 to 18 carbon atoms, and amine oxides having an alkyl group containing about 8 to about 24 carbon atoms and a methyl and/or ethyl group.

The bleaching agent compositions of the present invention may contain up to 80% by weight, preferably up to 50% by weight of the builders, up to 30% by weight, preferably up to 20% by weight of the anionic surfactants, and up to 30% by weight, preferably up to 20% by weight of the nonionic surfactants, based on the total weight of the compositions.

The enzymes which can be incorporated in the bleaching agent compositions of the present invention are hydrolases that promote the addition and removal of water, oxidoreductases that catalyze oxidation and reduction reactions, transferases that catalyze the transfer of a chemical group from one molecule to another to denature contaminants to promote removal thereof, synthetases and lyases that catalyze the cleavage of intermolecular linkages to decompose contaminants to promote removal thereof, and enzymes that chemically denature contaminants to promote removal thereof. Among these enzymes, hydrolases are preferred, and inter alia, proteases are most preferred. Examples of the proteases used herein include serine proteases, pepsin, trypsin, chymotrypsin, collagenase, keratanase, esterases, subtilisin, papain, carboxypeptidases A and B, and aminopeptidase. The preferred proteases are serin proteases. They are readily available as commercial products, for example, "Alkarase" from Novo Industries, "Esperase" from Novo Industries, "Viroprase" from Nagase Industries K.K., "Maxatase" from Guist Brokedes, "ALP-2" from Meiji Confectionary K.K., and
"Sperase" from Pfeizer.

The bleaching agent compositions of the present invention may preferably contain about 0.01 to about 5% by weight of the enzymes.

It should be noted that one or more of the activators defined above may be prepared in a granular form before they are blended with the peroxide according to the present invention. The activator may preferably be granulated by adding 5 to 200 parts by weight, more preferably 10 to 100 parts by weight of one or more binders which show fluidity at temperatures of 5° to 60° C., preferably 10° to 40° C. to 100 parts by weight of the activator and subjecting the mixture to a suitable granulating process.

The binders which can be used in granulating the activators are selected from nonionic surfactants, polyethylene glycol, polypropylene glycol, fluid paraffin, and higher alcohols, and mixtures thereof, provided that they show fluidity at temperatures of 5° to 60° C., preferably 10° to 40° C. Some preferred examples of the nonionic surfactants includes compounds (I) to (VI) shown below:

(I) polyoxyethylene alkyl or alkenyl ethers having an alkyl or alkenyl group containing on the average 10 to 20 carbon atoms and having 1 to 20 mols of ethylene oxide added;

(II) polyoxyethylene alkyl phenyl ethers having an alkyl group containing on the average 6 to 12 carbon atoms and having 1 to 20 mols of ethylene oxide added;

(III) polyoxypropylene alkyl or alkenyl ethers having an alkyl or alkenyl group containing on the average 10 to 20 carbon atoms and having 1 to 20 mols of propylene oxide added;

(IV) polyoxybutylene alkyl or alkenyl ethers having an alkyl or alkenyl group containing on the average 10 to 20 carbon atoms and having 1 to 20 mols of butylene oxide added;

(V) nonionic surfactants having an alkyl or alkenyl group containing on the average 10 to 20 carbon atoms and having in total 1 to 20 mols of ethylene oxide plus propylene oxide or ethylene oxide plus butylene oxide added wherein the ratio of ethylene oxide/propylene oxide or ethylene oxide/butylene oxide ranges from 1/99 to 99/1; and (VI) copolymers of ethylene oxide and propylene oxide, and ethylene oxide and butylene oxide.

Any well-known techniques may be employed for granulation including extrusion granulation, tumble granulation, and compression granulation and a proper choice depends on the type of the activator and the binder used, and other factors. For instance, the activator may be granulated by means of an extrusion granulator by previously finely dividing the activator to a particle size of less than about 150 μm, placing the powder activator in a well-known mixer, and gradually adding the binder to the mixer, thereby fully milling the powder activator and the binder. The milled mixture is then charged in the granulator to form granules which are then sifted. If desired, the granules emerging from the granulator may be coated with an inorganic fine powder having an average primary particle diameter of less than about 0.1 μm, for example, finely divided silica for the purpose of improving granule properties before they are subject to sifting.

The bleaching agent compositions of the present invention may preferably be blended with granular detergents to obtain bleaching detergent compositions. In this case, the activators used are preferably prepared in granular form by any of the above-described techniques.

The granular detergents used herein may be ordinary detergents intended for washing clothes. Typical detergents may contain any desired ones of ingredients [1]to [7]shown below and a proper choice depends on the intended application. The granular detergents may be prepared by spray drying a slurry containing the following ingredients into granules having a particle diameter of 200 to 500 μm and an apparent specific gravity of 0.15 to 0.40 g/ml. Any desired detergent ingredients may be dry blended with the resultant spray dried product.

[1] Surfactant (1) Straight or branched alkyl benzene sulfonates having an alkyl group having on the average 10 to 16 carbon atoms.

(2) alkyl or alkenyl ether sulfates having a straight or branched alkyl or alkenyl group containing on the average 10 to 20 carbon atoms and having added on the average 0.5 to 8 mols per molecule of ethylene oxide, propylene oxide or butylene oxide, or ethylene oxide plus propylene oxide in a molar ratio of 1/99 to 99/1 or ethylene oxide plus butylene oxide in a ratio of 1/99 to 99/1.

(3) alkyl or alkenyl sulfates having an alkyl or alkenyl group containing on the average 10 to 20 carbon atoms.

(4) olefin sulfonates having on the average 10 to 20 carbon atoms.

(5) alkane sulfonates having on the average 10 to 20 carbon atoms.

(6) saturated and unsaturated fatty acid salts having on the average 10 to 24 carbon atoms.

(7) alkyl or alkenyl ether carboxylates having a straight or branched alkyl or alkenyl group containing on the average 10 to 20 carbon atoms and having added on the average 0.5 to 8 mols per molecule of ethylene oxide, propylene oxide or butylene oxide, or ethylene oxide plus propylene oxide in a molar ratio of 1/99 to 99/1 or ethylene oxide plus butylene oxide in a molar ratio of 1/99 to 99/1.

(8) α-sulfofatty acid salts and esters represented by the general formula (i):

$$R^1-\underset{\displaystyle SO_3B}{\underset{|}{C}}HCO_2A \qquad (i)$$

wherein A is an alkyl group having 1 to 3 carbon atoms or a paired ion, B is a paired ion, and $R^1$ is an alkyl or alkenyl group having 10 to 20 carbon atoms. Examples of the ions include alkali metal ions such as sodium and potassium ions.

(9) polyoxyethylene alkyl or alkenyl ethers having an alkyl or alkenyl group containing on the average 10 to 20 carbon atoms and having 1 to 20 mols of ethylene oxide added.

(10) polyoxyethylene alkyl phenyl ethers having an alkyl group containing on the average 6 to 12 carbon atoms and having 1 to 20 mols of ethylene oxide added.

(11) polyoxypropylene alkyl or alkenyl ethers having an alkyl or alkenyl group containing on the average 10 to 20 carbon atoms and having 1 to 20 mols of propylene oxide added.

(12) polyoxybutylene alkyl or alkenyl ethers having an alkyl or alkenyl group containing on the average 10 to 20 carbon atoms and having 1 to 20 mols of butylene oxide added.

(13) nonionic surfactants having an alkyl or alkenyl group containing on the average 10 to 20 carbon atoms and having in total 1 to 30 mols of ethylene oxide plus propylene oxide or ethylene oxide plus butylene oxide added wherein the ratio of ethylene oxide/propylene oxide or ethylene oxide/butylene oxide ranges from 1/99 to 99/1.

(14) sucrose fatty acid esters of fatty acids having on the average 10 to 20 carbon atoms with sucrose.

(15) fatty acid glycerin monoesters of fatty acids having on the average 10 to 20 carbon atoms with glycerin.

(16) alkylamine oxides represented by the general formula (ii):

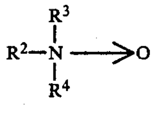
(ii)

wherein $R^2$ is an alkyl or alkenyl group having 10 to 20 carbon atoms, and $R^3$ and $R^4$ are alkyl groups having 1 to 3 carbon atoms.

(17) cationic surfactants represented by the general formulae (iii) to (v):

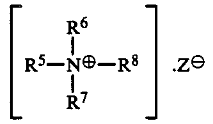
(iii)

wherein at least one of $R^5$, $R^6$, $R^7$, and $R^8$ is an alkyl or alkenyl group having 8 to 24 carbon atoms, and the remainings are alkyl groups having 1 to 5 carbon atoms, and Z is a halogen or methyl sulfate.

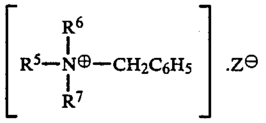
(iv)

wherein $R^5$, $R^6$, $R^7$, and Z are as defined above.

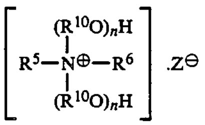
(v)

wherein $R^5$, $R^6$, and Z are as defined above, $R^{10}$ is an alkylene group having 2 to 3 carbon atoms, and n is an integer having a value of 1 to 20.

[2] Divalent metal ion trapping agents (1) Phosphoric acid salts such as orthophosphates, pyrophosphates, tripolyphosphates, metaphosphates, hexametaphosphates, and phytates.

(2) Phosphonic acid salts such as ethane-1,1-diphosphonic acid, ethane-1,2-triphosphonic acid, ethane-1-hydroxy-1,1-diphosphonic acid and derivatives thereof, ethanehydroxy-1,1,2-triphosphonic acid, ethane-1,2-dicarboxy-1,2-diphosphonic acid, and methanehydroxyphosphonic acid.

(3) Phosphonocarboxylic acid salts such as 2-phosphonobutane-1,2-dicarboxylic acid, 1-phosphonobutane-2,3,4-tricarboxylic acid, and α-methylphosphonosuccinic acid.

(4) Salts of amino acids such as glycine, aspartic acid, and glutamic acid.

(5) Aminopolyacetic acid salts such as nitrilotriacetates, ethylenediaminetetraacetates, and diethylenetriaminepentaacetates.

Preferred among the aforementioned salts (1) to (5) are alkali metal salts.

(6) High molecular weight electrolytes such as polyacrylic acid, polyfumaric acid, polymaleic acid, and poly(α-hydroxyacrylic acid).

(7) Salts of organic acids such as diglycollic acid, oxydisuccinic acid, carboxymethyloxysuccinic acid, citric acid, lactic acid, tartaric acid, oxalic acid, malic acid, gluconic acid, carboxymethylsuccinic acid, and carboxymethyltartaric acid. Their salts with alkali metals are preferred.

(8) Aluminosilicic acid salts represented by the general formula (vi):

$$x(M'_2O \text{ or } M''O).Al_2O_3.y(SiO_2).w(H_2O) \quad (vi)$$

wherein M' is an alkali metal, M" is an alkaline earth metal replaceable by potassium, x, y, and w represent the moles of the associated components, and generally, x has a value from 0.7 to 1.5, y has a value from 1 to 3, and w has any value, including crystalline and amorphous aluminosilicates and mixtures thereof.

[3] Alkaline agents or inorganic electrolytes

Salts of silicic acid and sulfuric acid, preferably with alkali metals.

[4] Recontamination inhibitors

Polyethylene glycol, polyvinyl alcohol, polyvinyl pyrrolidone, and carboxymethyl cellulose.

[5] Enzymes

Protease, lipase, amylase, and cellulase.

[6] Fluorescent dyes 4,4'-bis-(2-sulfostyryl)-biphenyl salts, 4,4'-bis-(4-chloro-3-sulfostyryl)-biphenyl salts, 2-(stilphenyl)naphthothiazole derivatives, 4,4'-bis(triazol-2-yl)stilbene derivatives, and bis(triazinylamino)stylbene disulfonic acid derivatives.

[7] Flavors and dyes

When the bleaching agent compositions of the present invention are blended with granular detergents to form bleaching detergent compositions, the resulting bleaching detergent compositions should preferably contain 1 to 95% by weight of the peroxides.

As described above, the present bleaching agent compositions comprising a peroxide capable of releasing hydrogen peroxide in aqueous solution, in admixture with an activator for the peroxide selected from the group consisting of naphthonitriles of formula (1), isophthalonitriles of formula (2), terephthalonitriles of formula (3), alkali metal salts of cyanic acid, cyanic acid ammonium salt, cyanopyridines of formula (4) and acid neutralized products thereof, cyanopyridinium salts of formula (5), O-acyl compounds of formula (6), and N-acyl compounds of formula (7) have an improved bleaching power and enable bleaching of an article within a short time.

Examples of the present invention are given below by way of illustration and not by way of limitation

EXAMPLE/COMPARATIVE EXAMPLE I

Bleaching agent compositions of Examples 1 to 9 and Comparative Examples 1 to 4 were prepared by blending sodium percarbonate or sodium perborate with the activators in varying molar ratios as shown in Table 1. These bleaching agent compositions were subjected to a bleaching test and a discoloration test as will be described below. The results are shown in Table 1.

It should be noted that "E" represents "Example" and "CE" represents "Comparative Example" in the following tables.

Bleaching test

Plain cotton cloth (#100) was washed at 50° C. for 15 minutes in a washing machine at a bath ratio of 30 folds using a commercial detergent (Blue Dia®), and then spin dried for 5 minutes. The cloth was again washed and dried by the same procedure. After the cloth was rinsed with overflowing water for 15 minutes, it was spin dried for 5 minutes. The procedure of overflow rinsing and drying was repeated five times in total and then, the cloth was dried in air, obtaining a pretreated cloth.

A 2% tea solution was boiled for 5 minutes. The pretreated cloth was immersed in the boiled tea solution at a bath ratio of 30 folds which was further boilded for 3 minutes and kept at 40° C. for 30 minutes. The cloth was removed and dried in air, obtaining a tea dyed cloth, that is, test cloth.

The bleaching agent compositions were added to tap water at 20° C. to form bleaching solutions having a concentration of the bleaching agent of 0.5%, to which 0.5% of polyoxyethylene nonyl phenyl ether ($\overline{P}=8$). The tea dyed cloth was immersed in the bleaching solution at a bath ratio of 100 folds and kept immersed for a predetermined time (30 minutes). The thus treated test cloth was spin dried for 1 minute, rinsed with overflowing water for 1 minute, and then spin dried for 1 minute in a washing machine. The cloth was then dried by ironing, obtaining a bleached cloth.

The pretreated cloth, tea dyed cloth, and bleached cloth were measured for reflectance by means of an optical reflectance photometer (ELREPHO, manufactured by Carl Zeiss). The bleaching effect was evaluated by the following equation:

$$\text{Bleaching effect} = (Rb - Rt)/(Rp - Rt) \times 100\%$$

wherein

Rp is the reflectance of the pretreated cloth,
Rt is the reflectance of the tea dyed cloth, and
Rb is the reflectance of the bleached cloth.

Discoloration test

Pieces of 7 cm by 7 cm were cut from cloth dyed with a given dye (Blue 27) and extended on square frames by pinning at the four corners. To each piece of dyed cloth, 10 grams of each of the bleaching detergent compositions of Examples and Comparative Examples was sprinkled and water was sprayed thereon. After 15 minutes standing, the pieces were washed with water and then dried in air. To determine the degree of discoloration, the dry cloth pieces were evaluated in accordance with the following criterion.

| Point | Observation |
|---|---|
| 3 | Those areas which had been in contact with the bleaching detergent were noticeably discolored and a number of spots were discernible. |
| 2 | Those areas which had been in contact with the bleaching detergent were discolored and spots were clearly discernible. |
| 1 | Those areas which had been in contact with the bleaching detergent were somewhat discolored and only a few spots were discernible. |
| 0 | Those areas which had been in contact with the bleaching detergent were not discolored at all and few spots were discernible. |

TABLE 1

| | Bleaching agent composition | | | Bleaching | Discolor- |
|---|---|---|---|---|---|
| | Peroxide | Activator | Ratio* | effect, % | ation |
| E 1 | sodium percarbonate | 1-naphthonitrile | 1:1 | 54 | 0 |
| E 2 | " | 1-naphthonitrile | 1:0.5 | 52 | 0 |
| E 3 | " | 1-naphthonitrile | 1:0.25 | 47 | 0 |
| E 4 | " | 2-naththonitrile | 1:1 | 56 | 0 |
| E 5 | " | 1,3-dicyanonapthalene | 1:1 | 57 | 0 |
| E 6 | " | 1-cyano-2-methyl-naphthalene | 1:1 | 48 | 0 |
| E 7 | sodium perborate | 2-naphthonitrile | 1:1 | 55 | 0 |
| E 8 | sodium percarbonate | isophthalonitrile | 1:1 | 52 | 0 |
| E 9 | " | terephthalonitrile | 1:1 | 49 | 0 |
| CE 1 | " | benzonitrile | 1:1 | 42 | 0 |
| CE 2 | " | phthalonitrile | 1:1 | 38 | 0 |
| CE 3 | " | TAED | 1:1 | 53 | 3 |
| CE 4 | " | none | — | 40 | 0 |

*Molar ratio of peroxide to activator

As evident from the data in Table 1, the present compositions wherein sodium percarbonate or sodium perborate is combined with naphthonitriles, isophthalonitriles, or terephthalonitriles exhibit a substantially improved bleaching power as compared with the activator-free composition of Comparative Example 4 and the compositions of Comparative Examples 1 and 2 wherein the activators used are benzonitrile and phthalonitrile which are aromatic nitriles other than the compounds of formulae (1) to (3). It is seen that the naphthonitriles, isophthalonitriles, an terephthalonitriles have a superior activating effect on the peroxides. It is also seen that the present compositions are less likely to cause discoloration of articles treated therewith as compared with the bleaching agent of Comparative Example 3 wherein the activator used is tetraacetylethylenediamine (TAED).

EXAMPLE/COMPARATIVE EXAMPLE II

Bleaching agent compositions of Examples 10 to 14 and Comparative Examples 5 to 7 were prepared by blending sodium percarbonate or sodium perborate with the activators in varying molar ratios as shown in Table 2. These bleaching agent compositions were subjected to the same bleaching and discoloration tests as in the preceding Examples except that the polyoxyethylene nonyl phenyl ether was not added in the bleaching test. The results are shown in Table 2.

TABLE 2

| | Bleaching agent composition | | | Bleaching | Discolor- |
|---|---|---|---|---|---|
| | Peroxide | Activator | Ratio* | effect, % | ation |
| E 10 | sodium percarbonate | potassium cyanate | 1:1 | 58 | 0 |
| E 11 | " | potassium cyanate | 1:0.5 | 53 | 0 |
| E 12 | " | potassium cyanate | 1:0.25 | 49 | 0 |
| E 13 | sodium perborate | sodium cyanate | 1:1 | 56 | 0 |
| E 14 | " | ammonium cyanate | 1:0.5 | 50 | 0 |
| CE 5 | sodium percarbonate | potassium thiocyanate | 1:1 | 30 | 0 |
| CE 6 | " | TAED | 1:1 | 53 | 3 |
| CE 7 | " | none | — | 40 | 0 |

As evident from the data in Table 2, the present compositions wherein sodium percarbonate or sodium perborate is combined with alkali metal salts or ammonium salts of cyanic acid exhibit a substantially improved bleaching power as compared with the composition of Comparative Example 5 wherein the activator used is potassium thiocyanate and the activator-free composition of Comparative Example 7. It is seen that the alkali metal and ammonium salts of cyanic acid have a superior activating effect on the peroxides. It is also seen that the present compositions are less likely to cause discoloration of articles treated therewith as compared with the bleaching agent of Comparative Example 6 wherein the activator used is TAED.

EXAMPLE/COMPARATIVE EXAMPLE III

Bleaching agent compositions of Examples 15 to 27 and Comparative Example 8 were prepared by blending sodium percarbonate or sodium perborate with the activators in varying molar ratios as shown in Table 3. These bleaching agent compositions were subjected to a bleaching test as will be described below. The results are shown in Table 3.

Bleaching test

A pretreated cloth and a tea dyed cloth were prepared by the same procedures as described in the preceding Example/Comparative Example I.

The bleaching agent compositions were added to tap water at temperatures shown in Table 3 to form bleaching solutions having a concentration of the bleaching agent of 0.5%. The tea dyed cloth was immersed in the bleaching solution at a bath ratio of 100 folds and kept immersed for a predetermined time (15 minutes). The thus treated test cloth was spin dried for 1 minute, rinsed with overflowing water for 1 minute, and then spin dried for 1 minute in a washing machine. The cloth was then dried by ironing, obtaining a bleached cloth.

The pretreated cloth, tea dyed cloth, and bleached cloth were measured for reflectance by means of an optical reflectance photometer (ELREPHO, manufactured by Carl Zeiss). The bleaching effect was evaluated by the same equation as above.

TABLE 3

| | Bleaching agent composition | | | Bleaching | effect, % |
|---|---|---|---|---|---|
| | Peroxide | Activator | Ratio* | @ 5° C. | @ 25° C. |
| E 15 | sodium percarbonate | 2-cyanopyridine | 1:1 | 40 | 80 |
| E 16 | " | 2-cyanopyridine | 1:0.5 | 38 | 67 |
| E 17 | " | 2-cyanopyridine | 1:0.25 | 30 | 50 |
| E 18 | " | 3-cyanopyridine | 1:1 | 33 | 55 |
| E 19 | " | 4-cyanopyridine | 1:1 | 36 | 54 |
| E 20 | " | 3-cyano-6-methylpyridine | 1:1 | 30 | 52 |
| E 21 | " | 3-cyano-6-ethoxypyridine | 1:1 | 25 | 49 |
| E 22 | sodium perborate | 2-cyanopyridine | 1:1 | 38 | 80 |
| E 23 | sodium percarbonate | 2-cyanopyridine hydrochloride | 1:1 | 39 | 80 |
| E 24 | " | 2-cyanopyridine hydrochloride | 1:0.5 | 39 | 65 |
| E 25 | " | 2-cyanopyridine hydrochloride | 1:0.25 | 30 | 49 |
| E 26 | " | 3-cyanopyridine sulfuric acid | 1:1 | 34 | 54 |
| E 27 | sodium perborate | 4-cyanopyridine sulfuric acid | 1:1 | 33 | 52 |
| CE 8 | sodium percarbonate | none | — | 17 | 34 |

*Molar ratio of peroxide to activator

As evident from the data of Table 3, the present compositions wherein sodium percarbonate or sodium perborate is combined with cyanopyridines or acid neutralized products of cyanopyridines exhibit a substantially improved bleaching power as compared with the composition of Comparative Example, proving that the cyanopyridines have a superior activating effect on the peroxides.

EXAMPLE/COMPARATIVE EXAMPLE IV

Bleaching agent compositions of Examples 28 to 36 and Comparative Examples 9 to 12 were prepared by blending sodium percarbonate or sodium perborate with the activators in varying molar ratios as shown in Table 4. These bleaching agent compositions were subjected to the same bleaching and discoloration tests as in Example/Comparative Example I. The results are shown in Table 4.

TABLE 4

| | Bleaching agent composition | | | Bleaching | Discolor- |
|---|---|---|---|---|---|
| | Peroxide | Activator | Ratio* | effect, % | ation |
| E 28 | sodium percarbonate | methyl-2-cyanopyridinium chloride | 1:1 | 54 | 0 |
| E 29 | " | methyl-2-cyanopyridinium chloride | 1:0.5 | 50 | 0 |
| E 30 | " | methyl-2-cyanopyridinium chloride | 1:0.25 | 49 | 0 |
| E 31 | " | propyl-2-cyanopyridinium bromide | 1:0.5 | 52 | 0 |
| E 32 | " | propyl-3-cyanopyridinium bromide | 1:0.5 | 47 | 0 |
| E 33 | " | propyl-4-cyanopyridinium bromide | 1:0.5 | 49 | 0 |
| E 34 | " | octyl-2-cyanopyridinium chloride | 1:0.5 | 45 | 0 |
| E 35 | " | stearyl-2-cyanopyridinium chloride | 1:0.5 | 44 | 0 |
| E 36 | sodium perborate | lauryl-4-cyanopyridinium phenyl sulfonate | 1:0.5 | 45 | 0 |
| CE 9 | sodium percarbonate | propylpyridinium chloride | 1:0.5 | 33 | 0 |
| CE 10 | " | lauryltrimethylammonium chloride | 1:0.5 | 25 | 0 |
| CE 11 | " | TAED | 1:1 | 53 | 3 |
| CE 12 | " | none | — | 40 | 0 |

*Molar ratio of peroxide to activator

As evident from the data in Table 4, the present compositions wherein sodium percarbonate or sodium perborate is combined with cyanopyridinium salts exhibit a substantially improved bleaching power as compared with the activator-free composition of Comparative Example 12 and the compositions of Comparative Examples 9 and 10 wherein the activators used are propylpyridinium chloride which is a pyridinium salt other than those of formula (5) a@a cationic surfactant. It is seen that the cyanopyridinium salts have a superior activating effect on the peroxides. It is also seen that the present compositions are less likely to cause discoloration of articles treated therewith as compared with the bleaching agent of Comparative Example 11 wherein the activator used is TAED.

EXAMPLE/COMPARATIVE EXAMPLE V

Bleaching agent compositions of Examples 37 to 58 and Comparative Examples 13 to 21 were prepared by blending sodium percarbonate or sodium perborate with the activators in varying molar ratios as shown in Table 5. These bleaching agent compositions were subjected to a bleaching test and a discoloration test as will be described below. The results are shown in Table 5.

Bleaching test

A pretreated cloth was prepared by the same procedure as described in Example/Comparative Example I.

A 0.5% tea solution was boiled for 5 minutes. The pretreated cloth was immersed in the boiled tea solution at a bath ratio of 30 folds which was then boilded for 3 minutes and allowed to stand at 40° C. for 30 minutes. The cloth was removed and dried in air, obtaining a tea dyed cloth, that is, test cloth.

The bleaching agent compositions were added to tap water at 20° C. to form bleaching solutions having a concentration of the bleaching agent of 0.5%, which was gently stirred for 30 seconds with a glass rod. The tea dyed cloth was immersed in the bleaching solution at a bath ratio of 100 folds and kept immersed for a predetermined time (60 minutes). The thus treated test cloth was spin dried for 1 minute, rinsed with overflowing water for 1 minute, and then spin dried for 1 minute in a washing machine. The cloth was then dried by ironing, obtaining a bleached cloth.

The pretreated cloth, tea dyed cloth, and bleached cloth were measured for reflectance by means of an optical reflectance photometer (ELREPHO, manufactured by Carl Zeiss). The bleaching effect was evaluated by the aforementioned equation.

Discoloration test

Pieces of cloth dyed with a given dye (Blue 27) were treated under the same conditions as used in the foregoing bleaching test. They were samples in this discoloration test. To determine the degree of discoloration, they were evaluated in accordance with the following criterion.

| Point | Observation |
|---|---|
| 3 | Noticeably discolored. |
| 2 | Uneven discoloration is observed. |
| 1 | Somewhat uneven discoloration is observed. |
| 0 | No discoloration. |

TABLE 5

| | Bleaching agent composition | | | Bleaching | Discolor- |
|---|---|---|---|---|---|
| | Peroxide | Activator | Ratio* | effect, % | ation |
| E 37 | sodium percarbonate | sodium hexanoyloxy-methane sulfonate | 1:1 | 72 | 0 |
| E 38 | " | sodium hexanoyloxy-methane sulfonate | 1:0.5 | 68 | 0 |
| E 39 | " | sodium hexanoyloxy-methane sulfonate | 1:0.3 | 65 | 0 |
| E 40 | " | sodium hexanoyloxy-methane sulfonate | 1:0.1 | 60 | 0 |
| E 41 | " | sodium octanoyloxy-methane sulfonate | 1:0.5 | 65 | 0 |
| E 42 | " | sodium octanoyloxy-methane sulfonate | 1:0.3 | 62 | 0 |
| E 43 | " | sodium nonanoyloxy-methane sulfonate | 1:0.5 | 65 | 0 |
| E 44 | " | sodium lauroyloxy-methane sulfonate | 1:0.5 | 61 | 0 |
| E 45 | " | sodium hexanoyloxy- | 1:0.5 | 70 | 0 |

TABLE 5-continued

| | Bleaching agent composition | | | Bleaching | Discolor- |
|---|---|---|---|---|---|
| | Peroxide | Activator | Ratio* | effect, % | ation |
| | | ethane sulfonate | | | |
| E 46 | " | sodium nonanoyloxy-ethane sulfonate | 1:0.5 | 70 | 0 |
| E 47 | " | sodium hexanoyloxy-phenyl methane sulfonate | 1:0.5 | 67 | 0 |
| E 48 | sodium perborate | sodium hexanoyloxy-methane sulfonate | 1:0.5 | 65 | 0 |
| E 49 | " | sodium hexanoyloxy-methane carboxylate | 1:0.5 | 62 | 0 |
| E 50 | " | sodium nonanoyloxysuccinate | 1:0.5 | 62 | 0 |
| E 51 | sodium percarbonate | sodium hexanoylamino-methane sulfonate | 1:0.5 | 68 | 0 |
| E 52 | " | sodium hexanoylamino-methane sulfonate | 1:0.3 | 62 | 0 |
| E 53 | " | sodium nonanoyl-N—methylaminomethane sulfonate | 1:0.5 | 67 | 0 |
| E 54 | " | sodium hexanoyl-N—methanolaminomethane sulfonate | 1:0.5 | 66 | 0 |
| E 55 | " | sodium hexanoyl-N—methyltaurine | 1:0.5 | 69 | 0 |
| E 56 | " | sodium octanoyl-N—methyltaurine | 1:0.5 | 66 | 0 |
| E 57 | " | sodium nonanoyl-N—methyltaurine | 1:0.5 | 66 | 0 |
| E 58 | " | sodium lauroyl-N—methyltaurine | 1:0.5 | 68 | 0 |
| CE 13 | " | sodium hexanoyloxy-propane sulfonate | 1:1 | 50 | 0 |
| CE 14 | " | sodium hexanoyloxy-propane sulfonate | 1:0.5 | 49 | 0 |
| CE 15 | " | sodium hexanoyloxy-butane sulfonate | 1:1 | 47 | 0 |
| CE 16 | " | sodium hexanoyloxy-aminopropane sulfonate | 1:1 | 49 | 0 |
| CE 17 | " | sodium hexanoyl-N—methylaminopropane sulfonate | 1:1 | 47 | 0 |
| CE 18 | " | TAED | 1:1 | 62 | 2 |
| CE 19 | " | TAED | 1:0.5 | 58 | 1 |
| CE 20 | " | PAG | 1:1 | 59 | 2 |
| CE 21 | " | none | — | 47 | 0 |

*Molar ratio of peroxide to activator

As evident from the data in Table 5, the present compositions wherein sodium percarbonate or sodium perborate is combined with O-acyl compounds of formula (6) or N-acyl compounds of formula (7) exhibit a substantially improved bleaching power as compared with the activator-free composition of Comparative Example 21 and the compositions of Comparative Examples 13 to 17 wherein the activators used are O and N-acyl compounds other than the compounds of formulae (6) and (7). It is seen that these activators have a superior activating effect on the peroxides. It is also seen that the present compositions are less likely to cause discoloration of articles treated therewith as compared with the bleaching agent compositions of Comparative Examples 18 to 20 wherein the activators used are TAED and pentaacetyl glucose (PAG).

EXAMPLE/COMPARATIVE EXAMPLE VI

Bleaching detergent compositions were prepared by homogeneously dry blending the granular detergent shown below with the bleaching agent compositions in the proportions as shown in Tables 6 and 7. They were subjected to a bleaching/cleaning test. The results are shown in Tables 6 and 7.

Granular detergent

The granular detergent used had the following composition.

| Ingredient | % by weight |
|---|---|
| LAS-Na(mixture of $C_9$ to $C_{14}$) | 8 |
| AS-Na(mixture of $C_{10}$ to $C_{14}$) | 2 |
| AOS-Na(mixture of $C_{14}$ to $C_{18}$) | 12 |
| Zeolite | 16 |
| Sodium silicate | 10 |
| Sodium carbonate | 8 |
| Soap(mixture of $C_{16}$ to $C_{18}$) | 1 |
| Tinopal CBS-X ® (Ciba Geigy) | 0.1 |
| Enzyme (Alkarase 2.0T ®, Novo Ind.) | 0.5 |
| Water | 5 |
| Sodium sulfate | balance |
| Total | 100.0% |

Bleaching/cleaning test

Pieces of pretreated cloth and tea dyed cloth were prepared by the same procedures as described in Example/Comparative Example I.

The bleaching detergent compositions were dissolved in tap water at 25° C. to form cleaning solutions having a concentration of the bleaching detergent composition of 0.75%. The tea dyed cloth pieces were immersed in the solution at a bath ratio of 100 folds and kept immersed for a predetermined time (30 minutes). After additional tap water was added to reduce the concentration of the bleaching detergent composition to 0.15%, washing was performed in a Terg-O-Tometer (manufactured by U.S. Testing) at 120 r.p.m. for 10 munutes. The thus treated test pieces were spin dried for 1 minutes, rinsed with overflowing water for 1 minute, and then spin dried for 1 minute in a washing machine. The test pieces were dried by ironing, obtaining bleached/cleaned cloth pieces.

The pieces of pretreated cloth, tea dyed cloth, and bleached/cleaned cloth were measured for reflectance by means of an optical reflectance photometer (ELREPHO, manufactured by Carl Zeiss). The bleaching effect was evaluated by the aforementioned equation.

TABLE 6

| | Bleaching agent composition | | Molar ratio of peroxide/ | Weight ratio of bleaching agent/ | Bleaching |
|---|---|---|---|---|---|
| | Peroxide | Activator | activator | granular detergent | effect, % |
| E 59 | sodium percarbonate | 1-naphthonitrile | 1:1 | 10/90 | 24 |
| E 60 | " | 1-naphthonitrile | 1:0.5 | 10/90 | 22 |
| E 61 | " | isophthalonitrile | 1:1 | 10/90 | 31 |
| E 62 | " | isophthalonitrile | 1:1 | 5/95 | 19 |
| E 63 | sodium perborate | isophthalonitrile | 1:0.5 | 10/90 | 27 |
| E 64 | sodium percarbonate | 2-cyanopyridine | 1:1 | 10/90 | 38 |
| E 65 | " | 3-cyanopyridine | 1:0.5 | 10/90 | 30 |
| CE 22 | " | — | — | 5/95 | 5 |
| CE 23 | " | — | — | 10/90 | 8 |
| CE 24 | — | — | — | 0/100 | 0 |

TABLE 7

| | Bleaching agent composition | | Molar ratio of peroxide/ | Weight ratio of bleaching agent/ | Bleaching |
|---|---|---|---|---|---|
| | Peroxide | Activator | activator | granular detergent | effect, % |
| E 66 | sodium percarbonate | sodium hexanonyloxymethane sulfonate | 1:0.3 | 10/90 | 23 |
| E 67 | " | sodium hexanonyloxymethane sulfonate | 1:0.3 | 5/95 | 17 |
| E 68 | sodium perborate | sodium hexanonyloxymethane sulfonate | 1:0.3 | 10/90 | 22 |
| E 69 | sodium percarbonate | sodium nonanoyltaurine | 1:0.3 | 10/90 | 22 |
| E 70 | " | sodium lauroyl-N—methyltaurine | 1:0.5 | 15/85 | 26 |
| CE 25 | " | — | — | 10/90 | 8 |
| CE 26 | " | — | — | 5/95 | 5 |
| CE 27 | — | — | — | 0/100 | 0 |

As evident from the data in Tables 6 and 7, the bleaching detergent compositions wherein the present bleaching agent compositions having sodium percarbonate or sodium perborate combined with the present activators are blended with the granular detergent exhibit a substantially improved bleaching power as compared with the activator-free compositions of Comparative Examples 22, 23, 25, and 26.

What is claimed is:

1. A bleaching agent composition comprising a peroxide capable of releasing hydrogen peroxide in aqueous solution, characterized in that the composition further comprises an activator for the peroxide, said activator being at least one member selected from the group consisting of a cyanopyridine of the formula:

(4)

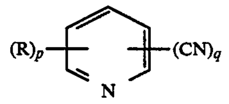

wherein R is a lower alkyl group or a lower alkoxy group, p has a value from 0 to 4, q has a value from 1 to 3, and the sum or p and q is from 1 to 5, inclusive;

an acid neutralized product of the cyanopyridine of formula (4); and a cyanopyridinium salt of the formula:

(5)

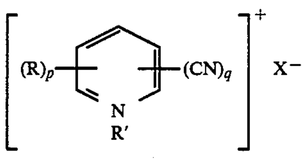

wherein R, p, and q are as defined above, R' is an alkyl or alkenyl group having 1 to 18 carbon atoms, and X is a halogen, an alkyl sulfonate group having 1 to 3 carbon atoms, or a phenyl sulfonate group.

2. The composition of claim 1 wherein the peroxide and the activator are blended in a molar ratio of from 20:1 to 1:2.

3. The composition of claim 1 wherein the peroxide is selected from the group consisting of hydrogen peroxide, percarbonates, perborates, and hydrogen peroxide adducts of pyrophosphates, citrates, sodium sulfate, urea and sodium silicate, and mixtures thereof.

4. The composition of claim 1 wherein the activator is a cyanopyridine of formula (4).

5. The composition of claim 1 wherein the activator is an acid neutralized product of the cyanopyridine of formula (4).

6. The composition of claim 5 wherein the acid of the neutralized product of the cyanopyridine of formula (4) is hydrochloric acid.

7. The composition of claim 5 wherein the acid of the neutralized product of the cyanopyridine of formula (4) is sulfuric acid.

8. The composition of claim 4 wherein the cyanopyridine is 2-cyanopyridine, 3-cyanopyridine or 4-cyanopyridine.

9. The composition of claim 8 wherein the cyanopyridine of formula (4) is 2-cyanopyridine.

10. The composition of claim 8 wherein the cyanopyridine of formula (4) is 3-cyanopyridine.

11. The composition of claim 8 wherein the cyanopyridine of formula (4) is 4-cyanopyridine.

12. The composition of claim 1 wherein the cyanopyridinium salt of formula (5) is a 2-cyanopyridine, 3-cyanopyridine, or 4-cyanopyridine salt of formula (5) wherein R′ is an alkyl group having 1 to 12 carbon atoms.

13. The composition of claim 1 wherein the activator is in granular form and is blended with the peroxide to form the composition.

14. The composition of claim 1 which contains an auxiliary additive selected from a builder, a surfactant, an enzyme, a flavor, a pigment, a fluorescent agent or mixtures thereof.

15. A bleaching detergent composition comprising a granular detergent and a bleaching agent composition as defined in claim 1.

16. The composition of claim 15 which contains an auxiliary additive selected from a surfactant, a divalent metal ion trapping agent, an alkaline agent, an electrolyte, recontamination inhibitor, an enzyme, a flavor, a dye or mixtures thereof.

* * * * *